(12) United States Patent
Yamamoto (10) Patent No.: US 11,761,941 B2
(45) Date of Patent: Sep. 19, 2023

(54) AUTOMATIC DETECTOR OF OILS AND MOLD ODORS, AND AUTOMATIC POISON MONITOR USING FISH WITH ODOR SENSOR

(71) Applicant: KANKYO ELECTRONICS CO.,LTD, Fukuoka (JP)

(72) Inventor: Takahiro Yamamoto, Fukuoka (JP)

(73) Assignee: KANKYO ELECTRONICS CO., LTD, Fukuoka (JP)

( * ) Notice: Subject to any disclaimer, the term of this patent is extended or adjusted under 35 U.S.C. 154(b) by 203 days.

(21) Appl. No.: 17/468,091

(22) Filed: Sep. 7, 2021

(65) Prior Publication Data

US 2022/0276214 A1    Sep. 1, 2022

(30) Foreign Application Priority Data

Sep. 9, 2020 (JP) ................. 2020-151411

(51) Int. Cl.
| | |
|---|---|
| *G01N 33/18* | (2006.01) |
| *G01N 27/12* | (2006.01) |
| *G01N 27/20* | (2006.01) |
| *G01N 29/036* | (2006.01) |
| *G01N 29/24* | (2006.01) |

(52) U.S. Cl.
CPC ............ *G01N 33/18* (2013.01); *G01N 27/12* (2013.01); *G01N 27/20* (2013.01); *G01N 29/036* (2013.01); *G01N 29/2437* (2013.01); *G01N 33/186* (2013.01)

(58) Field of Classification Search
CPC ........ G01N 33/18; G01N 27/12; G01N 27/20; G01N 29/036; G01N 29/2437; G01N 33/186; G01N 33/0016; G01N 33/1833; G01N 2291/014; G01N 2291/021; G01N 27/00
See application file for complete search history.

(56) References Cited

FOREIGN PATENT DOCUMENTS

| JP | H10-307095 A | 11/1998 |
|---|---|---|
| JP | 2018-044831 A | 3/2018 |
| JP | 2019-124643 A | 7/2019 |
| JP | 2020-034436 A | 3/2020 |

*Primary Examiner* — Tarun Sinha
(74) *Attorney, Agent, or Firm* — Nakanishi IP Associates, LLC

(57) ABSTRACT

The functions of the odor (smell, odor, reek etc. have the same meaning) detecting process with the same raw water includes two functions, that is: a function of detecting an odor by a downward substitution method that substitutes, in a sensor portion, heavy odorous substances to a bottom portion and light normal air to an upper portion by a four-stage humidity removal process in which high humidity air which is first generated in a vaporizing portion is made into medium-humidity air with a dehumidifying portion, which is then made into low-humidity air with a constant-temperature portion, and then two or more types of sensor elements are exposed to dry air at the sensor portion; and a second function of detecting poison using fish in a monitoring water tank, which is detected with another process such as surveillance camera, image processor, periphery controller and the like. The above two functions are compactly incorporated as an integrated type into a single cabinet.

8 Claims, 7 Drawing Sheets

AUTOMATIC DETECTOR OF OILS AND MOLD ODORS, AND AUTOMATIC POISON MONITOR USING FISH WITH ODOR SENSOR

DETAILED DESCRIPTION OF INVENTION

Technical Field

According to the Water Supply Act of Japan (hereinunder "Water Supply Act"), raw tap water such as river surface flowing water, lake water, groundwater, dam water etc. is continuously drawn into a water purifying plant to thereby supply safe tap water to citizens by water purification treatment. For that purpose, 51 items designated as poisons are sampled and inspected every month. However, since it is not known when poison will be mixed into the water purification plant that purifies continuous water, continuous monitoring using fish, in which it is assumed that poison is being mixed into a water inlet, is legally mandated. It can be said that, since the continuous water is always untested in a sampling inspection, the fish monitoring is legally mandated and is a necessary inspection method to ensure safety of the tap water.

Goldfish and river fish are bred in a water tank, and raw water is drawn in via a bypass, and observers conduct 24-hour visual monitoring. However, because of problems such as misunderstandings and oversights due to physical fatigue or lack of personnel, automatic poison monitors that automatically monitor fish have gradually become widespread. After the 2001 terrorist attacks in the United States, the Ministry of Health, Labour and Welfare of Japan pointed out the importance of further monitoring tap water as a response to domestic terrorist incidents, and thus was the impetus for automatic poison monitors which use fish, to attract attention and become widely used. In Japan, several companies manufacture and sell automatic poison monitors which use fish. However, the technologies of the analysis methods are independently developed by each manufacturer, where, for example, technologies such as image processing methods with surveillance cameras, action potential methods using electrodes, and oxygen amount measurement methods using bacteria are widespread.

However, in regards to quality accidents at water purification plants, there were more oil inflow accidents than poison mixing accidents, with cases such as kerosene being poured into rivers, cars falling into rivers thus causing oil to flow out, and oil spill accidents due to heavy rain. Therefore, as a countermeasure, water purification plants have oil content detectors installed at water intake ports.

Moreover, due to the abnormal weather of the past few years, the propagation of blue-green algae that produce moldy odor substances (moldy-smelling blue-green algae) has led to the detection of the mold odor geosmin and 2-methylisoborneol (hereinafter referred to as 2-MIB) at water purification plants of the waterworks facilities, and has led to many complaints nationwide from citizens that the tap water has a mold odor. Mold odor cannot be detected by the conventional tin oxide semiconductor sensor used to detect gas, alcohol etc., and the detection can be done only by the human nose and by gas chromatography of a mass analyzer. However, for the latter, it takes several hours by a special engineer until the analysis result is obtained, hence there is a problem due to responsiveness; moreover, the product is expensive, so gas chromatography has not been widely used. Water quality managers at water purification plants need to be quick to resolve complaints from citizens, so with a 24-hour shift they take turns sniffing with their noses every few minutes, and when they smell mold, they immediately put activated carbon into the raw water to remove the mold odor, but if the timing of putting in the activated carbon is delayed, it will lead to complaints. Another related issue was that even if there was no mold odor, it was not known when the mold odor would occur, and therefore activated carbon would be continuously put in, hence the cost of activated carbon would increase and the financial burden would increase. Development is desired because if the occurrence and termination of mold odor can be automatically notified, the physical burden on the water quality managers can be reduced and the financial burden can be minimized.

The technical issue of detecting mold odor is that there are a small number of citizens who can detect mold odor from tap water even at a minor concentration. Mold odor is also said to be the sensitive to noses peculiar to Japanese people, where Japan has a rainy season. Its minor concentration is said to be 5 Ng/L (5 PPT≈0.000005 mg/L) to 3 Ng/L, and with scientific instruments, can only be presently detected by gas chromatography of a mass analyzer. It is desired that a scientific instrument has good responsiveness, is able to accomplish 24-hour continuous unattended automatic inspection of mold odor by any person, and is inexpensive. Therefore, although companies are progressing in development, there are some issues. First, though mold odor test solutions are commercially available and easy to use, since the mold odor test solution is dissolved by a methanol solvent, there is no test water directly dissolved in fresh water such as pure water. Methanol is often detected by tin oxide semiconductor sensors and the like, which are widely used for detecting gas and alcohol. In the mold odor detection experiment, it is necessary to solve the problem of dissolving solid mold substances directly in water. Further, water utility companies whose mission is to supply safe tap water desire to accomplish labor force savings, installation space solutions, cost reductions etc., by including the function of the automatic poison monitor using fish and the function of detecting oil odor and mold odor, thereby integrating the two functions.

BACKGROUND ART

As an example of an accident in which poisonous substances were mixed into raw water such as river surface flowing water, lake water, groundwater, dam water etc., formaldehyde (a cancer-causing substance) was detected in the Japan's Tone River system in 2012. Water intake suspension measures affected 870,000 people. There is also a case where cyanide was detected in the groundwater of a certain ham factory, and products including ham were recalled from supermarkets nationwide, affecting the survival of the company. Poisonous substances innumerably include organochlorine compounds such as PCBs (polychlorinated biphenyls), harmful heavy metals such as mercury, cadmium, lead, zinc, and hexavalent chromium, as well as dioxin which is said to be the worst in history, and acute poisons such as potassium cyanide and pesticides. Also included is a possibility of complex poisonous property in which a chemical substance undergoes a chemical reaction with another substance in a river or the like and changes into a poisonous substance.

Public water supply and food factories are required to take the best measures such as promptly detecting the poisonous substances mixing in raw water and stopping water intake. For this purpose, the bioassay method for poisonous substance monitoring using fish (also called bio-test method)

has been widely recognized and used for a long time. Since the mixing of poisonous substances can be fatal to humans in some cases, the bioassay method is mandated to be installed in accordance with the Water Supply Act. Article 23, Paragraph 1 of the Water Supply Act stipulates an emergency stop of water supply, hence when learning that supplied water may harm human health, the water utility company must immediately stop the water supply and take measures to inform concerned persons that it is dangerous to use the water.

The penal provision (Article 52 of the Water Supply Act) strictly stipulates that criminal law such as imprisonment of up to 3 years or a fine of up to 3 million yen is applied to any person who violates the provision of Article 23, Paragraph 1. The bioassay method is stipulated by law as well and is an important facility for counter-terrorism. As an example of terrorism, in response to the maintenance of Narita International Airport, an incident where extremists put waste oil/poison into the Hokuso Water Purification Plant in Chiba Prefecture occurred in June 1978. In recent years, there was a case of a third party trespassing into and putting poisonous substances into a waterworks facility.

Although fish are bred in monitoring water tanks and visual monitoring and automatic poison monitors are widely in practical use, the types of water pollution accidents of raw water are overwhelmingly oil accidents, and Table 1 below (Japan Water Works Association, from the Abnormal Water Quality Monitoring and Countermeasures Guidelines 2019) shows a list of water pollution accidents and changes over fiscal years.

CITATION LIST

Patent Literature

[Patent Literature 1] JPH10-307095 A
[Patent Literature 2] JP 2018-044831 A
[Patent Literature 3] JP 2019-124643 A
[Patent Literature 4] JP 2020-034436 A

SUMMARY OF INVENTION

Technical Problem

For many years, the present inventor has been responsible for the research and development and practical application of an automatic poison monitor using Japanese rice fish. By including and integrating a function of detecting odorous substances into the water quality automatic poison monitor using Japanese rice fish, which is already in practical use for solving recent problems of the water supply manager such as the complaint of oil content inflow accident and mold odor, this automatic poison monitor using Japanese rice fish can contribute to the water utility in labor force saving, reduction of installation space, reduction of cost, etc. of raw water monitoring.

Currently, automatic oil content measurement methods that detect oil content include a hexane extraction method which measures the mass of substances extracted from hexane, an ultraviolet fluorescence method by ultraviolet irradiation, an Orgastor method which uses a polymer film,

TABLE 1

CHANGES OVER YEARS OF WATER COMPANIES, ETC.
THAT HAVE SUFFERED WATER POLLUTION ACCIDENTS, ACCORDING TO WATER POLLUTANT

| CONTAMINATION-CAUSING SUBSTANCE | FISCAL 2013 | | FISCAL 2014 | | FISCAL 2015 | | FISCAL 2016 | | FISCAL 2017 | |
|---|---|---|---|---|---|---|---|---|---|---|
| OILS | 96 | 67.1% | 40 | 44.0% | 76 | 57.6% | 61 | 45.9% | 106 | 61.3% |
| ORGANIC MATTER | 4 | 2.8% | 4 | 4.4% | 5 | 3.8% | 2 | 1.5% | 5 | 2.9% |
| TURBIDITY | 5 | 3.5% | 8 | 8.8% | 10 | 7.6% | 22 | 16.5% | 19 | 11.0% |
| ODOR | 2 | 1.4% | 3 | 3.3% | 6 | 4.5% | 4 | 3.0% | 1 | 0.6% |
| PH VALUE | 0 | 0.0% | 1 | 1.1% | 2 | 1.5% | 1 | 0.8% | 0 | 0.0% |
| PESTICIDES | 2 | 1.4% | 0 | 0.0% | 2 | 1.5% | 5 | 3.8% | 1 | 0.6% |
| INORGANIC MATTER | 5 | 3.5% | 3 | 3.3% | 1 | 0.8% | 1 | 0.8% | 2 | 1.2% |
| SURFACTANT | 2 | 1.4% | 0 | 0.0% | 1 | 0.8% | 1 | 0.8% | 6 | 3.5% |
| CHROMATICITY | 3 | 2.1% | 2 | 2.2% | 0 | 0.0% | 2 | 1.5% | 0 | 0.0% |
| NITRATE NITROGEN | 0 | 0.0% | 1 | 1.1% | 0 | 0.0% | 2 | 1.5% | 3 | 1.7% |
| AMMONIA NITROGEN | 18 | 12.6% | 20 | 22.0% | 19 | 14.4% | 13 | 9.8% | 11 | 5.4% |
| CHLORIDE ION | 0 | 0.0% | 0 | 0.0% | 1 | 0.8% | 2 | 1.5% | 2 | 1.2% |
| OTHER | 6 | 4.2% | 9 | 9.9% | 9 | 6.8% | 17 | 12.8% | 17 | 9.8% |
| TOTAL | 143 | | 91 | | 13 | | 133 | | 173 | |

NOTE)
LEFT COLUMN SHOWS THE NUMBER OF ACCIDENTS BY CONTAMINATION-CAUSING SUBSTANCE, AND RIGHT COLUMN SHOWS THE RATIO OF EACH ITEM TO WHOLE.
*THE NUMBER OF ACCIDENTS REPRESENTS ALL THAT OCCURED WITHIN THE FISCAL YEAR, AND WHEN ONE BUSINESS OPERATOR REPORTS MULTIPLE ACCIDENTS, EACH ONE IS COUNTED.
SOURCE: MINISTRY OF HEALTH, LABOUR AND WELFARE WEBSITE, FISCAL 2018 NATIONAL WATER SERVICE PERSONNEL MEETING MATERIAL

There have been many complaints about mold odors due to the abnormal weather over the last few years. Geosmin and 2-methylisoborneol (2-MIB), which have a mold odor, have been detected in the water purification plant of the waterworks facility due to the propagation of mold odor substance-producing blue-green algae (mold odor cyanobacteria) attributable to the abnormal weather. Therefore, it is desired to develop an integrated device that includes a function to detect oil odor and mold odor, in an automatic poison monitor using fish.

and a crystal vibration method that measures the odor molecular mass adsorbed to an odor-sensitive film. Further, examples of oil film detection methods include a relative permittivity method that detects floating oil as an oil film and a light reflection method that irradiates a water surface with light and measures reflected light, but either method is large in shape, expensive, and complicated in operability, and could not be included in and integrated with the automatic poison monitor using Japanese rice fish.

Once oil content gets into a water well, filtration pond or the like of a water purification plant, the residual oil odor could not be removed even if the oil content was cleaned, causing a problem with complaints of the oil odor of tap water. As long as the law stipulates the poisonous substance monitoring using fish, if a poison monitor using fish must be installed, including and integrating a function to detect oil odor and mold odor gives great advantages to the water quality manager of the water purification plant, in labor force saving, reduction of installation space, reduction of cost, and the like.

Further, regarding the mold odor, the mold odor is not caused by the mold itself, but a substance produced by algae and the like that propagate in dams, lakes, reservoirs, rivers etc. which are tap water sources. Pholmidium, Anabena, and the like are known as problematic types among cyanobacteria, and propagation of these produces geosmin and 2-MIB (2-methylisoborneol), which generate a mold odor.

The method of sniffing odorous substances dissolved in raw water such as river surface flowing water, lake water, groundwater, and dam water, which are the raw materials of tap water, is described in "AS-K-0120", where "warming a sample to about 40° C." is described in one sentence thereof. Further described therein regarding the odor test operation is the "Standard Methods for the Examination of Water", which also describes the "warming of the test water to 40 to 50° C. and vigorously shaking it". According to past findings and reaction rate methods, the factor that affects the reaction rate is the reaction humidity in addition to the catalyst, hence the raw water must be warmed to 40° C. to 50° C. in order to effectively detect odorous substances in the raw water. It can be understood that the odor cannot be detected unless the odorous substances in the water are separated and vaporized by vigorous shaking while being warmed.

However, the inventor has already confirmed the problem that vapor is generated when the raw water containing an odor is heated to 40° C. to 50° C., so that the vapor adheres to the surface of the sensor element and the sensor does not function. Further, it is thought that an air pump and an air stone can be used as an alternative to warming and vigorous shaking for separating and vaporizing odorous substances. In fact, at a certain water purification plant, it is confirmed that raw water is vaporized and persons-in-charge sniff the vaporized matter with their noses. Further, any products utilized for this must conform to the detection methods of "AS-K-0120" and "Standard Methods for the Examination of Water: Issued by Japan Water Works Association".

For solving the problem, it is necessary to select an inexpensive and easily available device that is a small general-purpose product and whose performance is guaranteed. In particular, it has been found that a tin oxide semiconductor sensor in a sensor element portion has a property of sensitively reacting to gas and oil odors, but also has a property of being not so sensitive to the mold odor generated from diatoms, where another sensitive film piezoelectric resonance sensor reacts more sensitively. It is considered that the oil odor is detected by the tin oxide semiconductor sensor, and the mold odor, together with the oil odor, can be detected by using two or more types of sensor elements of the sensitive film piezoelectric resonance sensor.

There is a problem that warming the raw water from 40° C. to 50° C. always generates a vapor, and any of the sensor elements are vulnerable to the vapor, so if the vapor adheres to the element surface, the detection function deteriorates and the sensor element reduces its detecting function and becomes non-functional. Due to this, it is desirable to remove the vaporized humidity of 95% or more at the time of generation and expose the sensor element portion to a humidity of 30% or less.

The molecular weight of 2-MIB of mold odor is 168, 99% of normal air is composed of nitrogen and oxygen, and nitrogen $N_2$ molecular weight ≈28 and oxygen $O_2$ molecular weight ≈32, totaling 60. Since the 2-MIB is simply considered to be a substance heavier than air, a system process for removing humidity while transferring the 2-MIB with the vapor by a so-called downward substitution is required.

The system process must be included together with the automatic poison monitor within the standard dimensions of one cabinet, and for that purpose, the process device must be miniaturized and maintenance must be taken into consideration. Further, in order to continuously perform 24-hour unattended monitoring, it is necessary to automatically remove the substances adhering to the sensor element surface and periodically clean the inside.

It has been found that, even if fish (for example, Japanese rice fish) in a monitoring water tank in the automatic poison monitor using fish is exposed to several kinds of oils (, because the oils remain floating on the water surface, the fish kept in the monitoring water tank neither die nor behave abnormally. It has also been found that, since geosmin and 2-MIB (2-methylisoborneol), which have a mold odor substance, do not affect fish, the current automatic poison monitor using fish cannot detect any oils and mold odor substances by the bioassay method.

As a detector of oil content in raw water, other companies have products using technologies such as the relative permittivity method that detects floating oil as an oil film, and the light reflection method that irradiates the water surface with light and measures the reflected light, as well as products such as the odor measuring device, but a product that is integrated with the automatic poison monitor using fish has not been found. Further, there is a publication describing the detection of mold odor substances in raw water, in which the pollutant-containing water is set to a certain pH, CD derivatives consisting of the following (I) to (V) are added as sensors, which are irradiated with ultraviolet rays, and the fluorescence intensity at a specific wavelength is measured to thereby detect and identify the contamination. The CD derivatives utilized are (I) 3-deoxy-3-(6-hydroxy-2-naphthamide)-BCD, (II) 3-deoxy-3-(3-hydroxy-2-naphthamide)-BCD, (Ill) 3-deoxy-3-(3-hydroxy-2-naphthamide)-γCD, (IV) 3-deoxy-3-(6-hydroxy-1-naphthamide)-γCD, and (V) 3-deoxy-3-(2-hydroxy-1-naphthamide)-αCD.

However, the above has not been put into practical use at present. The only method that can detect mold odor is gas chromatography of a mass analyzer, but this takes several hours for a specialist engineer to obtain an analysis result, causing a problem in view of responsiveness, and the product is expensive, so gas chromatography has not become widespread.

Solution to Problem

For solving the above problem, an automatic detector of oils and mold odors according to the first aspect of the present invention is characterized by comprising:
 a vaporizing portion that heats raw water in a raw water container to which the raw water is continuously supplied to thereby generate high-humidity air;
 a dehumidifying portion that turns the high-humidity air, which is generated by the vaporizing portion, into medium-humidity air;
 a constant-temperature portion that further turns the medium-humidity air, which is dehumidified by the dehumidifying portion, into low-humidity air; and a sensor portion that detects an odor by exposing a sensor element provided at a bottom portion inside a sensor case to the low-humidity air, which is dehumidified by the constant-temperature portion, with a downward substitution method that substitutes, inside the sensor case, heavy odorous substance air to the bottom portion and light normal air to an upper portion.

In the automatic detector of oils and mold odors according to the first aspect of the present invention, the automatic detector of oils and mold odors according to the second aspect of the present invention is characterized in that
the vaporizing portion includes: a water heater that heats the raw water, and an air stone that blows, with an air pump, air into the heated raw water in the raw water container, and vaporizes into the high-humidity air,
the dehumidifying portion includes: a vapor pipe in which the high-humidity air generated in the vaporizing portion flows, and a cooling water circulating pipe that surrounds the vapor pipe, thereby dehumidifying air to the medium-humidity air with cool water flowing in the cooling water circulating pipe with which the cool water is supplied from a cooler and circulates,
the constant-temperature portion includes, inside a case for the constant-temperature portion: a superheating pipe connected to the vapor pipe of the dehumidifying portion and having a diameter smaller than a diameter of the vapor pipe, and an air heater that superheats the medium-humidity air, which flows in the superheating pipe, to dehumidify the medium-humidity air into the low-humidity air, and
the sensor portion detects different odors of substances by exposing a plurality of sensor elements installed at the bottom portion inside a case for the sensor portion the low-humidity air.

In the automatic detector of oils and mold odors according to the second aspect of the present invention, the automatic detector of oils and mold odors according to the third aspect of the present invention is characterized in that
the plurality of sensor elements use a sensitive film piezoelectric resonance sensor and a tin oxide semiconductor sensor.

In the automatic detector of oils and mold odors according to the second or third aspect of the present invention, the automatic detector of oils and mold odors according to the fourth aspect of the present invention is characterized in that
the air stone of the vaporizing portion includes: a first flow meter that measures flow rate of the air supplied by the air pump, and a deodorizer that removes external odors from the air supplied by the air pump,
the air stone is installed under the water superheater, and is so configured to bring a large amount of bubbles into contact with a superheating metal portion of the water superheater for promoting warming and separating of odorous substances to thereby burst the bubbles on a water surface, and to cause the vaporized high-humidity air, which is generated at an air pressure at the time of many bubbles bursting, to flow into the vapor pipe of the dehumidifying portion.

In the automatic detector of oils and mold odors according to any one of the second to fourth aspects of the present invention, the automatic detector of oils and mold odors according to the fifth aspect of the present invention is characterized in that
the vapor pipe penetrates through the cooling water circulating pipe and has an outlet side inclined downward, the cooling water circulating pipe is of a circulation type in which cooling water from the cooler enters from a water inlet on a lower side at an outlet side of the vapor pipe, flows toward a water outlet at an upper side of an inlet side of the vapor pipe, and is returned to the cooler from the water outlet, thereby while the warm air in the vapor pipe flows from up to down, the cooling water reversely flows from down to up, which is a configuration increasing a cooling effect of the vapor pipe, the vapor pipe has a configuration in which the vapor pipe is exposed in a lower portion, and dew condensation water generated in the vapor pipe due to a difference in temperature from the cooling water is accumulated in the lower portion, and a drain pipe connected to a dew condensation accumulating port and an electromagnetic valve provided for the drain pipe automatically and periodically drain the dew condensation water, thereby obtaining the middle-humidity air, and the superheating pipe having a different diameter and being a small pipe is connected at the upper portion of the dew condensation accumulating port.

In the automatic detector of oils and mold odors according to the fifth aspect of the present invention, the automatic detector of oils and mold odors according to the sixth aspect of the present invention is characterized in that
the superheating pipe having the different diameter and being a small pipe is machined into an S shape to increase a heating area in the constant-temperature portion, and an air heater is installed in the lower portion of the superheating pipe and the air in the superheating pipe is kept at a set temperature by a temperature adjustment controller, to thereby make the air in the superheating pipe into the low-humidity air and expose the sensor element to the low-humidity air at the sensor portion.

In the automatic detector of oils and mold odors according to any one of the fourth to sixth aspects of the present invention, the automatic detector of oils and mold odors according to the seventh aspect of the present invention is characterized by comprising:
an air purge fan that blows fresh air through a deodorizer to the sensor element inside the case of the sensor portion and cleans the sensor element, and an electromagnetic valve that is located at a downstream side of the deodorizer and periodically opens and closes,
wherein the air is discharged from a top upper portion of the case of the sensor portion via a second flow meter.

An automatic poison monitor using fish with odor sensor according to the eighth aspect of the present invention is characterized in that the automatic detector of oils and mold odors according to any one of the first to seventh aspects of the present invention; and an automatic poison monitor using fish that detects a poison with a surveillance camera and an image processor for movement of fish, are compactly incorporated into a single cabinet as an integrated type.

Advantageous Effects of Invention

The automatic detector of oils and mold odors of the present invention, by being configured as described above, brings the following effects.

That is, with a downward substitution method that substitutes, in the sensor portion, the heavy odorous substance air to the bottom portion and the light normal air to the upper portion, the low-humidity air obtained by dehumidifying the high-humidity air, which is generated by first heating at the vaporizing portion, by the dehumidifying portion and the constant-temperature portion, is exposed to the sensor element provided at the bottom portion inside a sensor case, making it possible to efficiently detect the odor contained in the raw water.

Further, by providing the air stone that blows the air, with the air pump, to the heated raw water in the raw water container in order to vaporize the air into the high-humidity air, the odorous substances can be separated and vaporized, thereby enhancing the odor detection effect.

Further, the dehumidifying portion is provided with the vapor pipe in which the high-humidity air generated in the vaporizing portion flows, and a cooling water circulating pipe surrounding the vapor pipe, so that air can be more efficiently dehumidified to the medium-humidity air by cool water flowing in the cooling water circulating pipe with which the cool water is supplied from the cooler and circulates.

Further, the constant-temperature portion includes, inside a case of the constant-temperature portion, the superheating pipe connected to the vapor pipe of the dehumidifying portion, the superheating pipe having a diameter smaller than that of the vapor pipe, and the air heater that superheats the medium-humidity air flowing through the superheating pipe, thereby making it possible to dehumidify the medium-humidity air into the low-humidity air.

Further, exposing the low-humidity air to a plurality of sensor elements installed at the bottom portion inside the case of the sensor portion enables the sensor portion to detect different odors of substances.

Further, by using, as a plurality of sensor elements, a sensitive film piezoelectric resonance sensor and a tin oxide semiconductor sensor, oil odor and mold odor can be simultaneously detected.

Further, providing the air stone of the vaporizing portion with the deodorizer that removes external odors from the air supplied by the air pump can remove the external odors.

Further, the air stone is installed in the lower portion of the water superheater, and bringing a large amount of bubbles in contact with the superheating metal portion of the water superheater can promote warming and separating of odorous substances, and at the same time, can thereby burst the bubbles on the water surface and can cause the vaporized high-humidity air, which is generated at the air pressure at the time of a large number of bubbles bursting, to flow into the vapor pipe of the dehumidifying portion.

Further, the vapor pipe penetrates through the cooling water circulating pipe and has an outlet side inclined downward, and the cooling water circulating is of a circulation type in which the cooling water from the cooler enters from the water inlet on the lower side at the outlet side of the vapor pipe, flows toward the water outlet at the upper side of the inlet side of the vapor pipe, and is returned to the cooler from the water outlet, thereby, while the warm air in the vapor pipe flows from up to down, the cooling water reversely flows from down to up, thus making it possible to increase the cooling effect of the vapor pipe.

Further, the vapor pipe has a configuration in which the vapor pipe is exposed in the lower portion, and the dew condensation water generated in the vapor pipe due to the difference in temperature from the cooling water is accumulated in the lower portion, and the drain pipe connected to the dew condensation accumulating port and the electromagnetic valve provided for the drain pipe automatically and periodically drain the dew condensation water, and the superheating pipe having a different diameter small pipe is connected at the upper portion of the dew condensation accumulating port, thereby making it possible to efficiently send the medium-humidity air to the constant-temperature portion.

Further, machining the superheating pipe having a different diameter small pipe into an S shape and installing the air heater below the superheating pipe increases the heating area in the constant-temperature portion, making it possible to accomplish an efficient heating in a narrow space.

Further, providing the air purge fan that blows fresh air through the deodorizer to the sensor element inside the case of the sensor portion can clean the sensor element.

Further, providing the downstream side of the deodorizer with the electromagnetic valve that periodically opens and closes can prevent the air from entering through the air purge port, while the air purge fan is stopped.

Further, by making constant the air flow rate of the first flow meter of the air pump that sends the air to the vaporizing portion, and the air flow rate of the second flow meter provided on the top upper portion of the case of the sensor portion, it can be confirmed that the air reaches the sensor portion without leaking during the process.

The automatic poison monitor using fish with odor sensor of the present invention, being configured as described above, can bring about the following effects.

That is, automatic detection of odors which is the process device that can detect oil odor and mold odor is included in and integrated with the automatic poison monitor using fish which is referred to as the bioassay method that detects mixing of poisonous substances in raw tap water etc., thereby making it possible to accomplish labor force saving, reduction of installation space, reduction of cost, and the like, and to contribute to the safety of tap water and the comfortable eating habit.

DESCRIPTION OF EMBODIMENTS

The present invention will be described below with reference to the drawings.

Example 1

Figure 1:
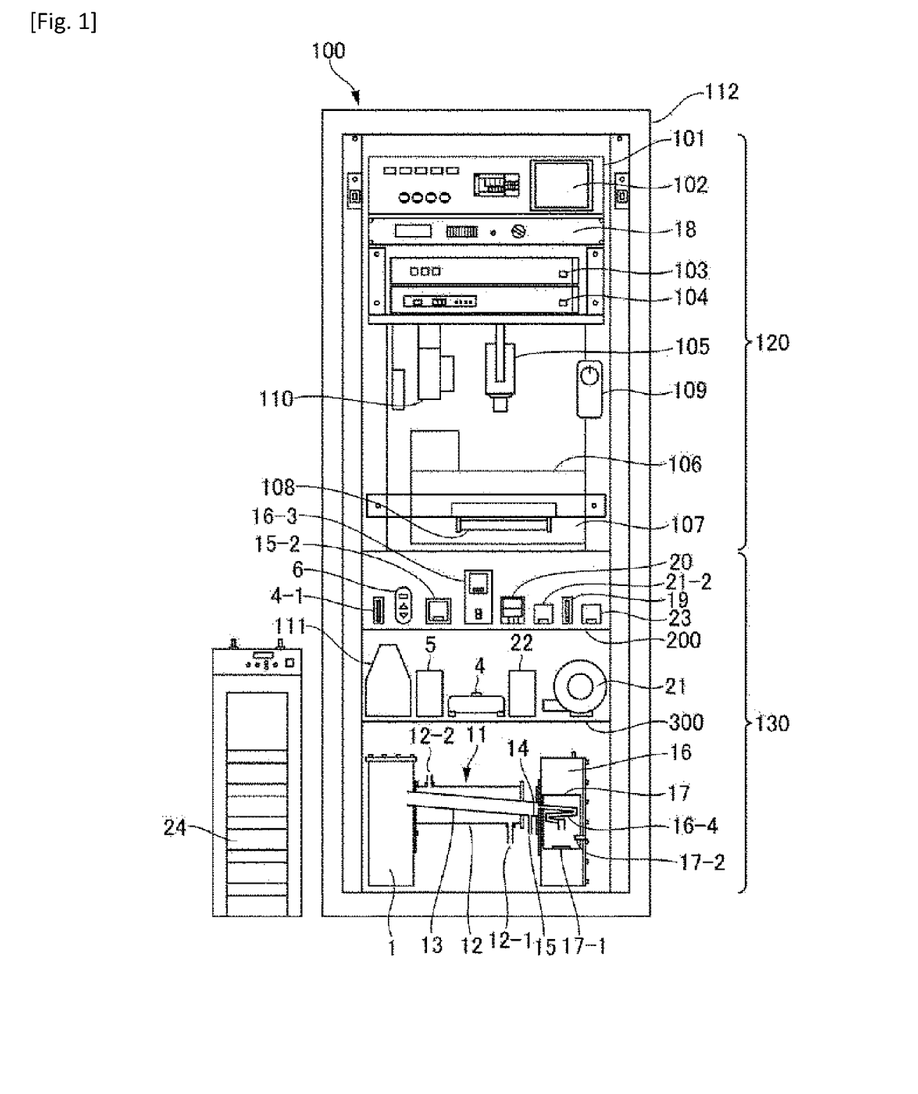
FIG. 1 is a configuration diagram of a device arrangement in which an odor-detecting function included in a cabinet of an automatic poison monitor using fish with odor sensor according to a first embodiment is integrated.

As shown in FIG. 1, an automatic poison monitor using fish 100 with odor sensor according to a first embodiment has a cabinet 112 that is a mass-produced product of EIA standard and is lightweight but has a high rigidity and an anti-seismic structure, and the front, rear, left and right faces can be opened and closed, and therefore is excellent in equipment installation and maintainability. The upper half of the cabinet 112 houses an automatic poison monitor using fish 120, and the lower half houses an automatic detector of oils and mold odors 130 which serves a function of detecting odors. The dimensions of the cabinet 112 include width 700 mm, height 1800 mm, depth 700 mm, and the cabinet 112 is a mass-produced standard product having a single-sided door with an acrylic plate on the front, and both the left and right sides and the back side are openable. However, any other standard product or a uniquely-designed cabinet may be used.

First, the upper half, that is, the automatic poison monitor using fish 120 will be described. A monitoring water tank 106 is installed in the lower stage of the upper half, and 15 to 20 of the fish 107, which are orange aquarium-bred Japanese rice fish, are constantly bred in the water tank. Natural Japanese rice fish (scientific name *Oryzias*) are described in the Red List Threatened Species II (VU) (Japan's Ministry of the Environment, Red List) and is a rare fish that cannot be caught, while orange aquarium-bred Japanese rice fish, being a farmed fish, is not subject to the above stipulation. Orange aquarium-bred Japanese rice fish is so easy to breed that they have been designated as a test fish in the poisonous property guidelines of the OECD (Organization for Economic Co-operation and Development), and there are cases of survival of up to 5 years. Unlike other fish species, orange aquarium-bred Japanese rice fish become adult fish in about half a year after hatching, and do not increase in size, and hence are the most suitable fish species as a test fish which do not change their reaction to poisons.

A large amount of raw water such as river surface flowing water, lake water, groundwater, and dam water is drawn into a water purification plant, where some of the raw water is repeatedly poured into and drained from the monitoring water tank 106 at a constant water volume by means of a bypass, and thereby the fish such as the orange aquarium-bred Japanese rice fish 107 and the like are constantly exposed to the raw water; therefore, if any poisonous substance is contained in the raw water, the orange aquarium-bred Japanese rice fish 107 exhibit abnormal behavior such as stopped behavior, repellent behavior, madness behavior, nose-raising behavior, and swarming, depending on the type and concentration of the poison.

A lighting fixture 108 is installed in front of the monitoring water tank 106, and a transparent acrylic plate for illuminating the lighting underwater is fitted in the monitoring water tank as a light-through-window. If there is no lighting, the imaging of a surveillance camera will be hindered. The reason why the lighting fixture is not installed at the upper portion of the water tank is that when the water surface is illuminated, the image processing is disturbed by the shaking of the water.

In order for the orange aquarium-bred Japanese rice fish to live well in case of an emergency, an automatic feeder 110 automatically feeds them once or twice a day, and the water temperature of the monitoring water tank 106 is kept constant year-round with a heater and a thermostat 109; air is supplied by a pump, and further, the raw water is gently circulated in the water tank to thereby activate the orange aquarium-bred Japanese rice fish and clean the water tank. Such a habitat is the most important thing to be aware of because mortality due to habitat deterioration makes the raw water poison monitoring unreliable.

The analysis of abnormal behavior is performed by photographing the fish with a CCD video camera 105 installed in the upper portion of the monitoring water tank 106 and sending the video signal to an image processor 104, where dozens of blocks are placed on a video screen and each block comprises a function to detect movement of the orange aquarium-bred Japanese rice fish, thereby analyzing the abnormal behavior by counting the number of detection blocks. Since there are many erroneous judgments in the analysis of abnormal behavior of fish, a periphery controller 103 divides one image of the CCD video camera 105 into four images, changes the analysis level of abnormal behavior for each of the four images, and controls four-stage alarm; and a control panel 101 wraps up monitoring such as with a monitor television 102 that displays the image of orange aquarium-bred Japanese rice fish, the four-stage alarm, device failure monitoring, the water temperature display monitoring etc. The alarm of the control panel 101 can be output as an alarm signal to the outside.

Next, the lower half, that is, the automatic detector of oils and mold odors 130 will be described with reference to FIG. 2 and FIG. 3.

A vaporizing portion 1 is provided with three connecting pipes including a raw water inlet 8, a drain port 7, and a dust removal port 9, which are respectively provided with a manual valve 8-1, a manual valve 7-1, and a manual valve 9-1; an air stone 2 and a water heater 3 are installed in the vaporizing portion, and a large amount of bubbles from the air stone 2 pass through the water heater 3 to be warmed. Thereby, the odorous substances are separated, the rise of bubbles is accelerated, and the bubbles burst on the water surface, thus making it easier to vaporize odorous substances. The vapor generated in the vaporizing portion 1 is called high humidity air and is set as a first stage with a humidity of 95% or more.

Air is supplied to the air stone 2 from an air pump 4 through a deodorizer 5 and a flow meter 4-1. Since the air pump 4 sucks any surrounding miscellaneous odors, it is necessary to remove the miscellaneous odors with the deodorizer 5. Concerning the water heater 3, "AS-K-0120" describes the "warming of a sample to about 40° C.". Concerning the test operation of odor, the "Standard Methods for the Examination of Water" also describes the "warming of test water to 40 to 50° C., and vigorously shaking it". The effect of "vigorously shaking" was to bring a large amount of generated bubbles of the porous air stone 2 into contact with a heating metal portion of the water heater 3. Installing the two water heaters 3 reduces the dimensions, a thermostat 6 with a set temperature in the range of 45° C. to 55° C. is provided, and a sensor 6-1 that transmits the water temperature to the thermostat is installed in water to thereby control the water temperature. The flow meter 4-1 sets the air supply amount to a constant level, and the air flow rate can be visually confirmed.

Figure 6:
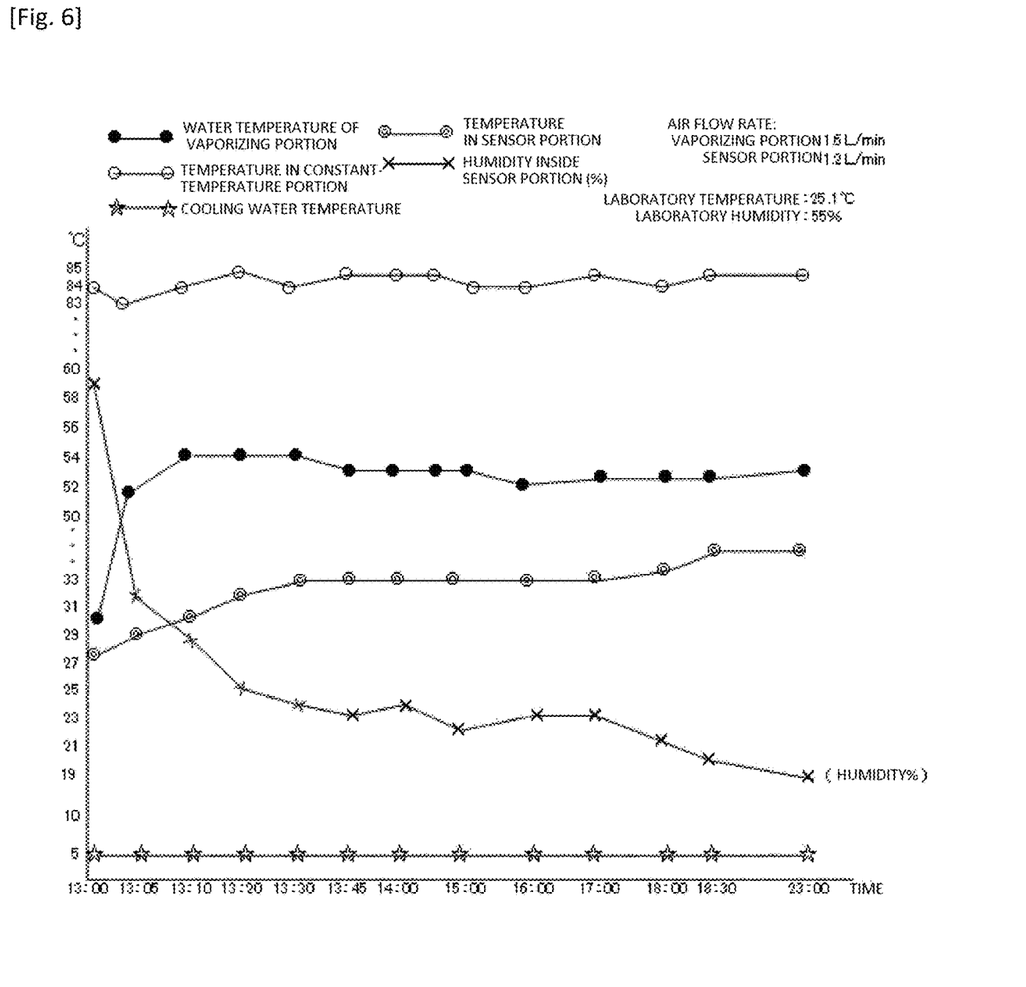
FIG. 6 is humidity test data.

As shown in the humidity test data in FIG. 6, the air supply amount is 1.6 L/min. Further, since it was confirmed from past cases that strange odors enter from sewage through a drainage port, these odors were blocked with a water seal 10.

In a dehumidifying portion 11, the tip end of a cooling water circulating pipe 12 is fixed to the upper portion of the vaporizing portion 1, and a vapor pipe 13 penetrates the inside of the cooling water circulating pipe 12. The tip end of the through port is above the water surface of the vaporizing portion 1 and is in a position where the raw water does not flow in. As shown in FIG. 6, the water heater 3 of the vaporizing portion 1 heats the raw water in the range of 45° C. to 55° C., and the odorous substances contained in the raw water are agitated by bubbles to be separated and vaporized. A large amount of bubbles burst on the water surface to thereby generate a wind pressure, which causes the high-humidity air to flow into the vapor pipe 13. The vapor pipe 13 is inclined downward.

The cooling water circulating pipe 12 has a structure in which the cooling water of a cooler 24 is supplied from a water inlet 12-1 on the lower side, enters and flows toward a water outlet 12-2 on the upper side; water bubbles adhering to the surface of the vapor pipe 13 in a structure in which the vapor flows from up to down while the cooling water reversely flows from down to up, can weaken the cooling function, but this structure can suppress the generation of water bubbles and enhance the cooling function.

Since dew condensation is generated on the entire surface of the cooling water circulating pipe 12 and falls as water droplets, a tray for the dew condensation water is installed in the lower portion of the cooling water circulating pipe 12 and a drainage pipe is provided in the lower portion of the tray. The cooling water from the water outlet 12-2 is returned to the cooler 24. The cooling water supplied from the cooler 24 has a circulation structure in which the cooling water passes through the cooling water circulating pipe 12 and returns to the cooler 24. The cooler 24 has a tank and a pump inside, and the refrigerant is R134 and is air-cooled, so storing the refrigerant in the cabinet 112 causes a ventilation problem, and thus the cooler 24 has to be installed outside the cabinet 112. Though the maximum cooling capacity of the cooler was −15° C., however, in the embodiments, continuous use was possible at 5° C., as shown in FIG. 6.

The vapor pipe 13, in the downward portion, is exposed from the cooling water circulating pipe 12, and is, on the terminal side, connected and fixed to a superheating pipe 16-4 narrower in diameter than the vapor pipe 13. The vapor pipe 13 and the superheating pipe 16-4 is a structure in which a step arises due to the difference in the thickness of the pipe, and is such that the dew condensation water accumulates between the steps, and the dew condensation water is accumulated in a dew condensation accumulating port 14 in the lowermost portion of the vapor pipe 13, but the drain pipe is connected and the drain pipe is provided with an electromagnetic valve 15-1; from a dew condensation water drain port 15, the dew condensation accumulated water is drained with an electromagnetic valve 15-1 opened at a set time by a timer relay 15-2. The vapor pipe 13 is directed downward also for a downward substitution; for smoothly transferring the odorous substances to the next step, for preventing the cooling effect from being reduced by removing the water bubbles on the surface of the vapor pipe 13 with the cooling water directed from downward to upward, and for smoothly draining the condensed water, where this is a second stage of the middle-humidity air.

The superheating pipe 16-4 which is narrow and different in diameter from the vapor pipe 13 is connected and fixed to the side face of a constant-temperature portion 16. An air heater 16-1 is installed on the bottom portion side inside the constant-temperature portion 16, and the internal temperature of the constant-temperature portion 16 is adjusted to a constant set temperature by the temperature transmitted from the sensor provided in a temperature adjustment controller 16-3 which is installed for this purpose. The superheating pipe 16-4 is provided in the upper portion of the air heater 16-1. The superheating pipe 16-4 is machined into an S shape as a method of increasing the area in order to increase the thermal efficiency. The superheating pipe 16-4 is always downwardly oriented by the downward substitution, and the low-humidity air containing the odor inside the heating pipe 16-4 is a third stage in which the low-humidity air flows downward. Even having removed the vapor moisture with the vapor pipe 13, the superheating pipe 16-4 has a humidity of 60% or more, and with this humidity, the sensor element surface is covered with moisture and the sensor function deteriorates, so the air must be low-humidity air. Further, the superheating pipe 16-4 is required for facilitating the downward flow of 2-MIB having a mold odor heavier than air.

According to the humidity test data table in FIG. 6, the temperature inside the constant-temperature portion 16 for causing the humidity to be 30% or less was 85° C. The superheating pipe 16-4 is inserted from the side face of the constant-temperature portion 16 to the side face of a sensor portion 17, and the tip end portion of the superheating pipe faces the bottom face and the 2-MIB mixed with the dry air is also discharged. With this stage as a fourth stage, the downward substitution occurs, and the heavy 2-MIB remains on the bottom face and the light normal air moves to the upper portion. Two types of sensors, a tin oxide semiconductor sensor 17-2 sensitive to oil odor and a sensitive film piezoelectric resonance sensor 17-1 sensitive to mold odor, are installed as sensor elements installed at the bottom portion. Depending on the substance to be detected, two or more types of sensors may be installed.

Air is discharged from one place on a ceiling face of the sensor portion 17, with a flow meter 19 being installed here, and if the air flow rate of the flow meter 4-1 of the air pump 4 and the air flow rate of the flow meter 19 of the sensor portion 17 are constant, it is considered that the air sent out from the air pump 4 has arrived at the sensor portion 17 without any air leakage during the process.

According to FIG. 6, it can be said that the air flow rate of the flow meter 4-1 at the inlet of the vaporizing portion 1 is 1.6 L/min, and the flow meter 19 at the outlet of the sensor portion is 1.2 L/min, each of which showing no change, therefore, there is no air leakage. A difference of 0.4 L/min is considered to be caused as the loss during heat exchange between processes and during the draining of the dew condensation water from the dew condensation accumulating port 14. A sensor 20-1 of a thermo-hygrometer 20 is installed in the sensor portion 17, making it possible to constantly confirm the temperature and humidity inside the sensor portion. According to FIG. 6, 20 minutes after starting operation, the temperature of the sensor portion reaches 32° C. and the humidity of the dry air reaches 25%, so it can be said that the four-step dehumidification process is effectively working. In the starting procedure, sequential operations need to be taken such that the cooler 24 is first started, the circulation of the cool water of 5° C. is confirmed in the cooling water circulating pipe 12, the temperature of the constant-temperature portion 16 is confirmed to be 85° C. or higher, and finally the water heater 3 of the vaporizing portion 1 and the air pump 4 for generating bubbles of the air stone 2 are started.

Figure 2:
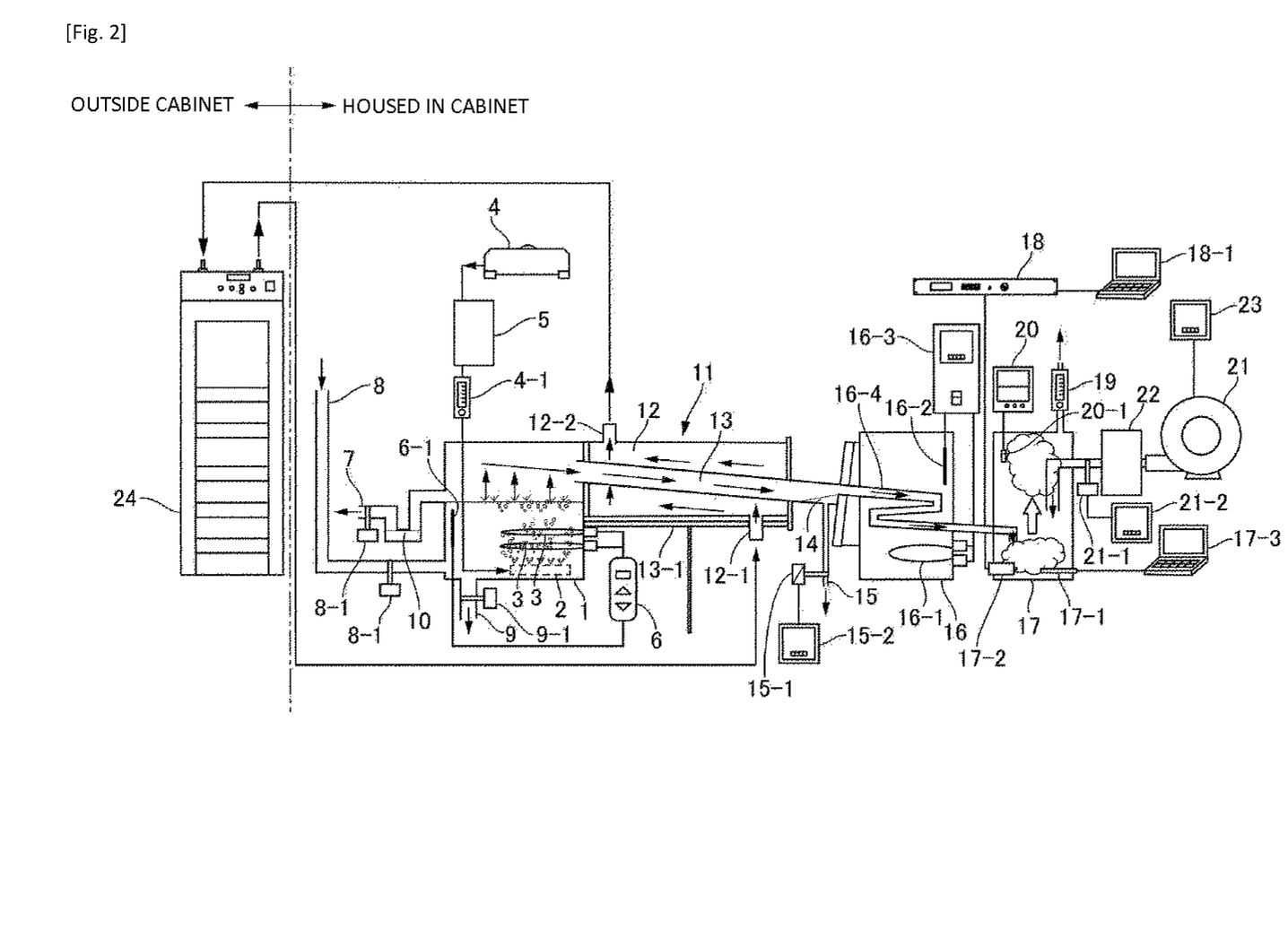
FIG. 2 is a configuration diagram of a process of the odor-detecting function of the automatic poison monitor using fish with odor sensor according to the first embodiment.
Figure 3:
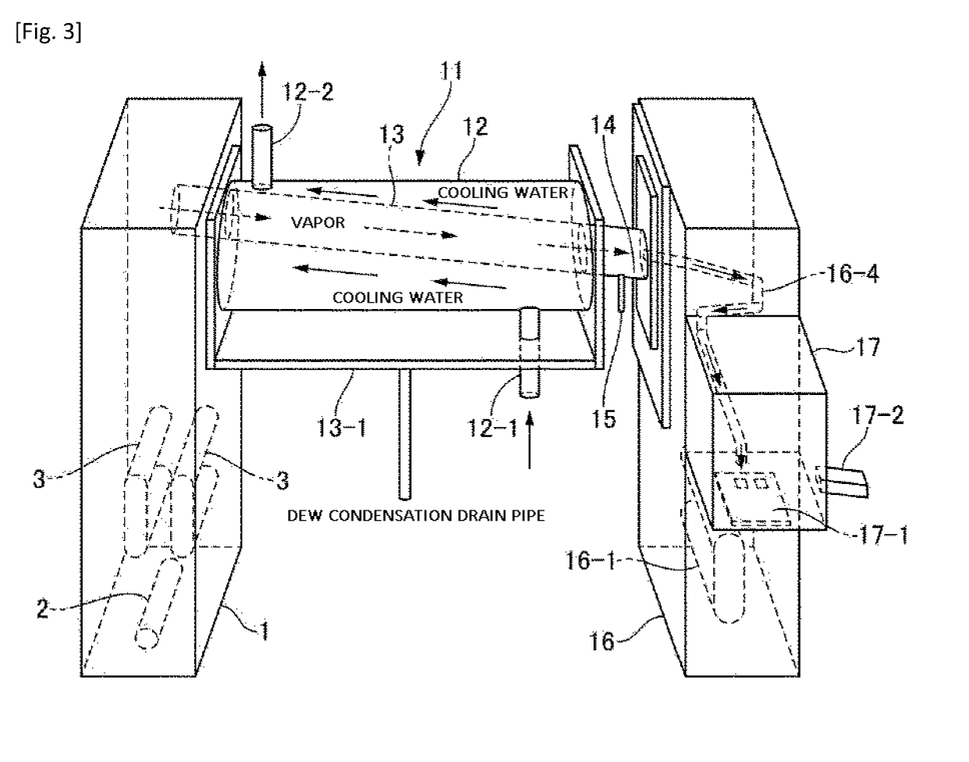
FIG. 3 is a perspective view of a process device for odor detection of the automatic poison monitor using fish with odor sensor according to the first embodiment.

FIG. 2 shows that the constant-temperature portion 16 and the sensor portion 17 are separated from each other and connected by the superheating pipe 16-4, but practically, the sensor portion 17 is brought into close contact with the front face of the constant-temperature portion 16, as shown in the perspective view of FIG. 3, forming a structure such that the internal temperature of the superheating pipe 16-4 does not change due to exposure.

It is considered that the temperature and humidity of the sensor portion have optimum set values for the odorous substances to be detected. Changing the set values can be performed by adjusting the amount of bubbles ejected from the air stone 2 of the vaporizing portion 1, adjusting the temperature of the water heater 3, adjusting the cooling temperature of the cooler 24, adjusting the temperature of the air heater 16-1 of the constant-temperature portion 16, and the like.

The principle of the tin oxide semiconductor sensor 17-2 of the sensor portion 17 is to measure the change in thermal conductivity and the change in electrical conductivity due to gas adsorption on the tin oxide ($SnO_2$) semiconductor surface, as a change in the resistance value of the platinum wire coil. By means of the current flowing through the platinum wire coil, the $SnO_2$ semiconductor, which is kept at about 300 to 450° C. adsorbs oxygen molecules on the surface, captures electrons, and has a high resistance value. When the reducing gas is adsorbed there, the electrons captured by the oxidation reaction are released into the $SnO_2$ semiconductor and the resistance value decreases. This change in resistance value is detected in association with the odor. The oil odor has been tested with kerosene, gasoline, light oil, heavy oil, and the like, but detection has been confirmed even with a small amount of oil.

Figure 7:
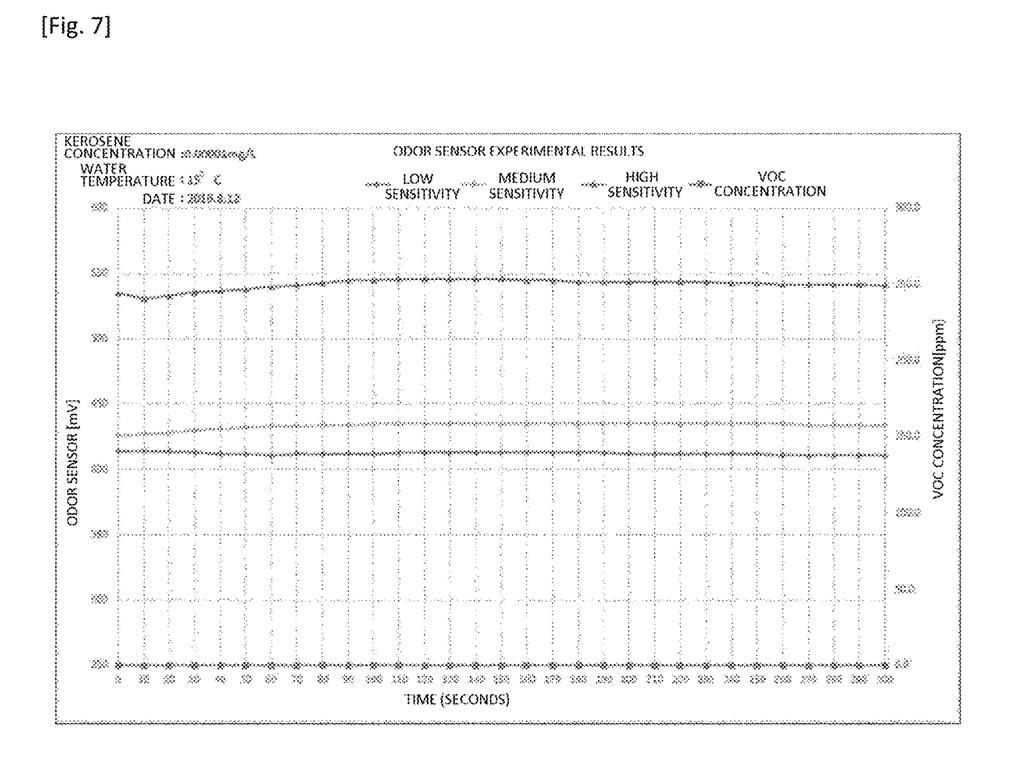
FIG. 7 is a detection test table with a 0.00001 concentration of kerosene.

FIG. 7 is a detection test table with a 0.00001 concentration of kerosene, and it can be seen that all of the three lines (high-sensitivity setting, medium-sensitivity setting, and low-sensitivity setting) from the top of FIG. 7 are detected.

Figure 5:
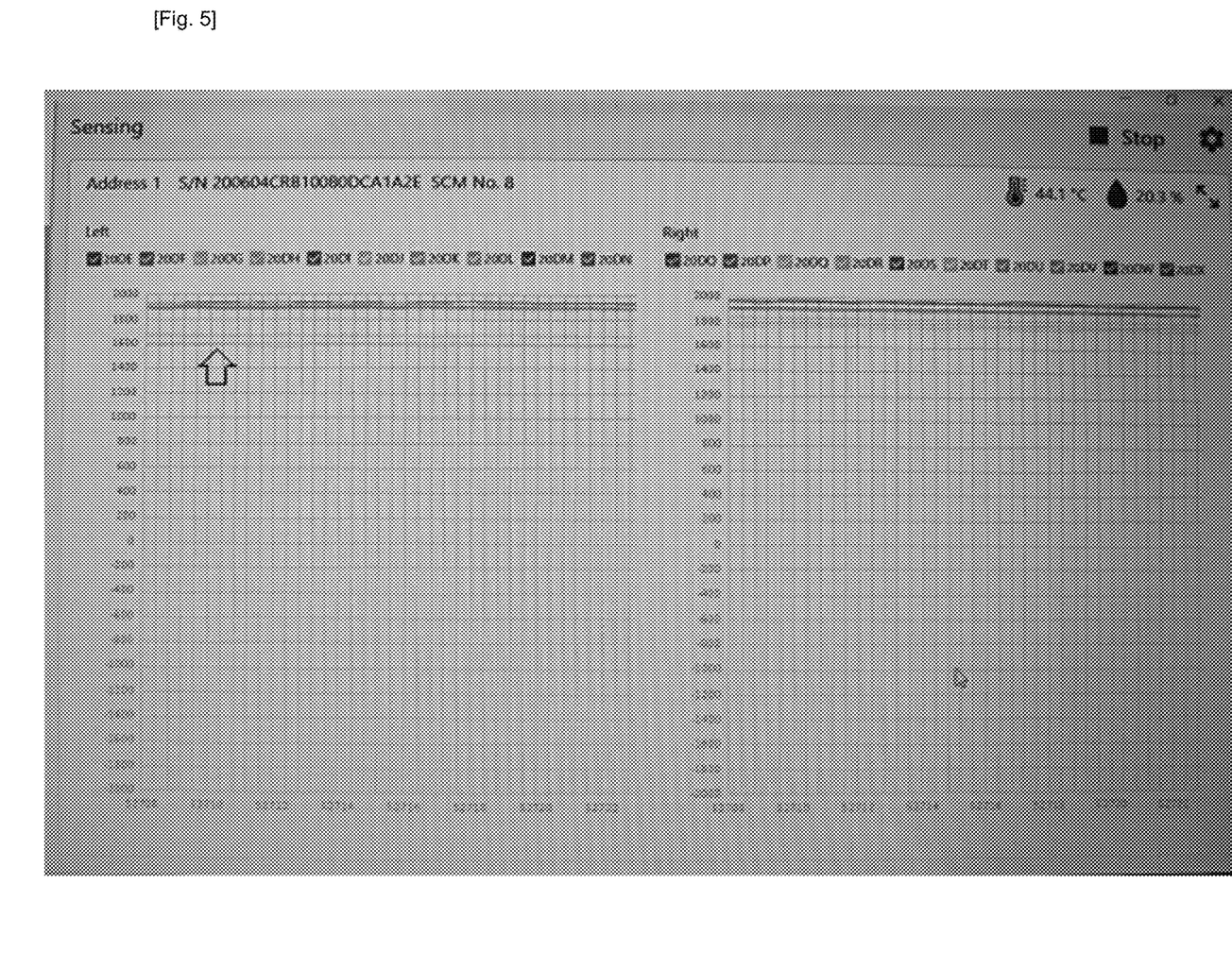
FIG. 5 is a photograph showing a personal computer screen which is a detection test result of detecting a mold 2-MIB concentration of 5 Ng/L in the automatic detector of oils and mold odors of the first embodiment.

In the detection test of the mold odor 2-MIB, the tin oxide semiconductor sensor did not react at 5 Ng/L (5 PPT≈0.000005 mg/L), but the sensitive film piezoelectric resonance sensor 17-1 detected it, and the personal computer screen that made the detection shows in FIG. 5 that only one of the many sensitive membranes is moving (arrow). Although a mold test solution is commercially available, the mold test solution is not used because the mold test solution is dissolved in a methanol solvent; the mold test water of the example can dissolve the solid mold substance in water by the ultrasonic vibration developed by our company; so our company was capable of manufacturing the present test water, and received an inspection certificate from a chemical analysis company certifying that the 2-MIB was 5 Ng/L (5 PPT≈0.000005 mg/L), and the thus manufactured test water was used. The principle of the sensitive film piezoelectric resonance sensor 17-1 is that several types of detection elements in which different sensitive films are applied to a piezoelectric thin film of lead zirconate titanate, the detection elements are mounted on a single sensor chip, odorous molecules are made to attach to the sensitive film that is resonating by applying voltage, and the odor is identified from the change in resonance frequency.

In the present invention, in order to perform 24-hour continuous unattended automatic monitoring, deposits on the surface of the sensor element and the inside of the sensor portion 17 must be periodically cleaned by air purge; otherwise it becomes difficult to detect new odors. Therefore, an air purge fan 21 is installed, and in order to start or stop the rotation of the fan, a timer relay 23 periodically performs the air purge at a set time. A deodorizer 22 is provided on the blowing side of the air purge fan 21, and the air with the external odor removed is used for the air purge. An electromagnetic valve 21-1 is installed at the outlet of the deodorizer 22 and opens at the same time as starting the air purge and closes at the same time as completing the air purge, and installing the electromagnetic valve prevents air intrusion from the air purge port during stoppage.

The materials of the vaporizing portion 1, the dehumidifying portion 11, the constant-temperature portion 16, and the sensor portion 17 in the perspective view of FIG. 3 were made by cutting a transparent acrylic plate with a thickness of 5 mm and adhering it with an adhesive for exclusive use, and a rubber plate was laid on an inspection port, followed by bolting. The cooling water circulating pipe 12 of the dehumidifying portion 11 utilized was an acrylic pipe with an outer diameter of 90 mm and a wall thickness of 3 mm, and the vapor pipe 13 utilized had an outer diameter of 35 mm and a wall thickness of 2 mm. The test operation period was about one month, of which the continuous operation was performed for two weeks, but no inconvenience such as the breakage or damage of acrylic nor water leakage was found. The transparent acrylic plate has advantages such as being able to see the inside and being easy to machine, but the heat resistant temperature is 79 to 90° C., and a durability test in the continuous operation test for at least one year is required. For example, instead of the acrylic material, other resin material with different properties, such as a resin having a strong heat resistance such as polycarbonate (heat resistant temperature 120 to 130° C.) may be used, or a metal material may be used.

Figure 4:
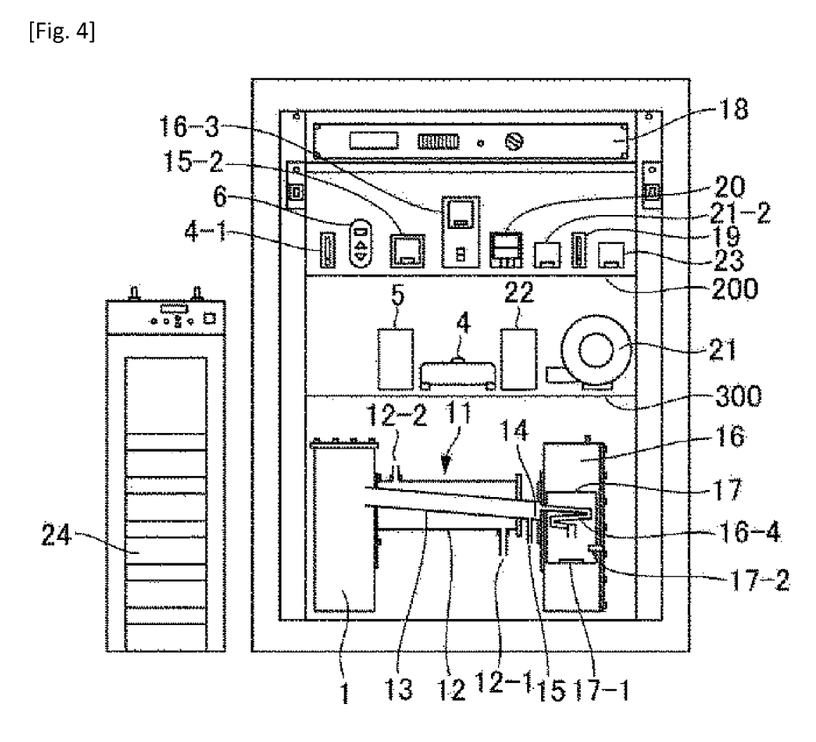
FIG. 4 is a configuration diagram showing a stand-alone device in which an automatic detector of oils and mold odors of the first embodiment is incorporated into a small cabinet.

As shown in FIG. 4, only the function of the automatic poison detector of oils and mold odors 130 composed of the vaporizing portion 1, the dehumidifying portion 11, the constant-temperature portion 16, the sensor portion 17, the accessory devices such as the water heater 3, the air heater 16-1, the air stone 2, the air pump 4, the electromagnetic valve 21-1, the manual valve 8-1, the air purge fan 21 and the deodorizer 22, various instruments and controllers, a personal computer 17-3, and the like can be separated from the automatic poison monitor using fish 120 and thereby can be, as a single function of odor detection only, incorporated into the small cabinet, but the process may also become large scale in the case of inspecting a large water volume. Further, housing in the cabinet may not be possible depending on the installation conditions; in such a case, the operation may be performed in an open state. Further, the layout of each device in FIG. 1 and FIG. 4 may be changed if there is no operational problem despite any change of the place or change of device under circumstances, for example, installing the water circulating portion in the lower portion, the electronic device portion in the upper portion etc., due to the inspection, the maintenance, and the electrical standard.

INDUSTRIAL APPLICABILITY

In the present invention, a detector of odors 130 which is a process device that can detect oil odor and mold odor, is included in and integrated with an automatic poison monitor using fish 120 which is referred to as the bioassay method that detects mixing of poisonous substances in raw tap water etc., which enables labor force saving, reduction of installation space, reduction of cost and the like, and can contribute to the safety of tap water and the comfortable eating habit, and thereby is applicable to water business companies as well as industrial fields that use water such as drinking water makers and food makers.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims. The entire disclosure of Japanese Patent Application No. 2020-151411 filed on Sep. 9, 2020 including specification, claims, drawings and summary is incorporated herein by reference in its entirety.

REFERENCE SIGNS LIST

100 Automatic poison monitor using fish with odor sensor
101 Control panel
102 Monitor television
103 Peripheral controller
104 Image processor
105 CCD video camera
106 Monitoring water tank
107 Orange aquarium-bred Japanese rice fish
108 Lighting fixture
109 Thermostat
110 Automatic feeder
111 Sampling water container
112 Cabinet
120 Automatic poison monitor using fish
130 Automatic detector of oils and mold odors
1 Vaporizing portion
2 Air stone
3 Water heater
4 Air pump
4-1 Flow meter
5 Deodorizer
6 Thermostat
6-1 Sensor
7 Drain port
8 Raw water inlet
8-1 Manual valve
9 Dust removal port
9-1 Manual valve
10 Water seal
11 Dehumidifying portion
12 Cooling water circulating pipe
12-1 Water inlet
12-2 Water outlet
13 Vapor pipe
13-1 Dew condensation tray
14 Dew condensation accumulating port
15 Dew condensation water drain port
15-1 Electromagnetic valve
15-2 Timer relay
16 Constant-temperature portion
16-1 Air heater
16-2 Sensor
16-3 Temperature adjustment controller
16-4 Superheating pipe
17 Sensor portion
17-1 Sensitive film piezoelectric resonance sensor
17-2 Tin oxide semiconductor sensor
17-3 Personal computer
18 Tin oxide semiconductor sensor controller
18-1 Personal computer
19 Flow meter
20 Thermo-hygrometer
20-1 Sensor
21 Air purge fan
21-1 Electromagnetic valve
21-2 Timer relay
22 Deodorizer
23 Timer relay
24 Cooler
200 Meter housing shelf
300 Device housing shelf

The invention claimed is:

1. An automatic detector of oils and mold odors, comprising:
   a vaporizing portion that heats raw water in a raw water container to which the raw water is continuously supplied to thereby generate high-humidity air;
   a dehumidifying portion that turns the high-humidity air, which is generated by the vaporizing portion, into medium-humidity air;
   a constant-temperature portion that further turns the medium-humidity air, which is dehumidified by the dehumidifying portion, into low-humidity air; and
   a sensor portion that detects an odor by exposing a sensor element provided at a bottom portion inside a sensor case to the low-humidity air, which is dehumidified by the constant-temperature portion, with a downward substitution method that substitutes, inside the sensor case, heavy odorous substance air to the bottom portion and light normal air to an upper portion.

2. The automatic detector of oils and mold odors according to claim 1, wherein
   the vaporizing portion includes: a water heater that heats the raw water, and an air stone that blows, with an air pump, air into the heated raw water in the raw water container, and vaporizes into the high-humidity air,
   the dehumidifying portion includes: a vapor pipe in which the high-humidity air generated in the vaporizing portion flows, and a cooling water circulating pipe that surrounds the vapor pipe, thereby dehumidifying the high-humidity air to the medium-humidity air with cool water flowing in the cooling water circulating pipe with which the cool water is supplied from a cooler and circulates,
   the constant-temperature portion includes, inside a case for the constant-temperature portion: a superheating pipe connected to the vapor pipe of the dehumidifying portion and having a diameter smaller than a diameter of the vapor pipe, and an air heater that superheats the medium-humidity air, which flows in the superheating pipe, to dehumidify the medium-humidity air into the low-humidity air, and
   the sensor portion detects different odors of substances by exposing a plurality of sensor elements installed at the bottom portion inside a case for the sensor portion to the low-humidity air.

3. The automatic detector of oils and mold odors according to claim 2, wherein
   the plurality of sensor elements use a sensitive film piezoelectric resonance sensor and a tin oxide semiconductor sensor.

4. The automatic detector of oils and mold odors according to claim 2, wherein
   the air stone of the vaporizing portion includes: a first flow meter that measures flow rate of the air supplied by the air pump, and a deodorizer that removes external odors from the air supplied by the air pump, and
   the air stone is installed under the water superheater, and is so configured to bring a large amount of bubbles into contact with a superheating metal portion of the water superheater for promoting warming and separating of odorous substances to thereby burst the bubbles on a water surface, and to cause the vaporized high-humidity air, which is generated at an air pressure at the time of many bubbles bursting, to flow into the vapor pipe of the dehumidifying portion.

5. The automatic detector of oils and mold odors according to claim 2, wherein the vapor pipe penetrates through the cooling water circulating pipe and has an outlet side inclined downward, the cooling water circulating pipe is of a circulation type in which cooling water from the cooler enters from a water inlet on a lower side at an outlet side of the vapor pipe, flows toward a water outlet at an upper side of an inlet side of the vapor pipe, and is returned to the cooler from the water outlet, thereby while the warm air in the vapor pipe flows from up to down, the cooling water reversely flows from down to up, which is a configuration increasing a cooling effect of the vapor pipe, the vapor pipe has a configuration in which the vapor pipe is exposed in a lower portion, and dew condensation water generated in the vapor pipe due to a difference in temperature from the cooling water is accumulated in the lower portion, and a drain pipe connected to a dew condensation accumulating port and an electromagnetic valve provided for the drain pipe automatically and periodically drain the dew condensation water, thereby obtaining the middle-humidity air, and the superheating pipe having a different diameter and being a small pipe is connected at the upper portion of the dew condensation accumulating port.

6. The automatic detector of oils and mold odors according to claim 5, wherein the superheating pipe having the different diameter and being a small pipe is machined into an S shape to increase a heating area in the constant-temperature portion, and an air heater is installed in the lower portion of the superheating pipe and the air in the superheating pipe is kept at a set temperature by a temperature adjustment controller, to thereby make the air in the superheating pipe into the low-humidity air and expose the sensor element to the low-humidity air at the sensor portion.

7. The automatic detector of oils and mold odors according to claim 4, comprising:

an air purge fan that blows fresh air through a deodorizer to the sensor element inside the case of the sensor portion and cleans the sensor element, and an electromagnetic valve that is located at a downstream side of the deodorizer and periodically opens and closes, wherein the air is discharged from a top upper portion of the case of the sensor portion via a second flow meter.

8. An automatic poison monitor using fish with an odor sensor, wherein the automatic detector of oils and mold odors according to claim 1; and an automatic poison monitor using fish that detects a poison with a surveillance camera and an image processor for movement of fish, are compactly incorporated into a single cabinet as an integrated type.

\* \* \* \* \*